(12) United States Patent
Schwarz

(10) Patent No.: US 11,800,982 B2
(45) Date of Patent: Oct. 31, 2023

(54) PROBE INCLUDING A SEAL WITH A PLEATED FLEXIBLE MEMBRANE FOR OPTOACOUSTIC IMAGING OF AN OBJECT, AND SYSTEM AND METHOD FOR THE SAME

(71) Applicant: ITHERA MEDICAL GMBH, Munich (DE)

(72) Inventor: Mathias Schwarz, Munich (DE)

(73) Assignee: ITHERA MEDICAL GMBH, Munich (DE)

(*) Notice: Subject to any disclaimer, the term of this patent is extended or adjusted under 35 U.S.C. 154(b) by 185 days.

(21) Appl. No.: 16/558,565

(22) Filed: Sep. 3, 2019

(65) Prior Publication Data

US 2020/0069189 A1 Mar. 5, 2020

(30) Foreign Application Priority Data

Sep. 4, 2018 (EP) ..................................... 18192394

(51) Int. Cl.
*A61B 5/00* (2006.01)
*A61B 8/00* (2006.01)

(52) U.S. Cl.
CPC .......... *A61B 5/0095* (2013.01); *A61B 8/4494* (2013.01); *A61B 2576/00* (2013.01)

(58) Field of Classification Search
CPC . A61B 5/0095; A61B 8/4494; A61B 2576/00; A61B 2562/168; A61B 5/0064;
(Continued)

(56) References Cited

U.S. PATENT DOCUMENTS

| 2006/0272419 A1* | 12/2006 | Maris | G01N 29/0681 |
| | | | 430/5 |
| 2011/0166455 A1* | 7/2011 | Cully | A61B 8/4245 |
| | | | 600/463 |

(Continued)

FOREIGN PATENT DOCUMENTS

| EP | 0327347 A2 * | 8/1989 | ............... B62D 3/12 |
| EP | 2742853 | 6/2014 | |

(Continued)

OTHER PUBLICATIONS

Extended Search Report for European Patent Application No. 18192394.7, dated Feb. 19, 2019, 10 pages.

(Continued)

*Primary Examiner* — Christopher Koharski
*Assistant Examiner* — Richmond J Van Winter
(74) *Attorney, Agent, or Firm* — Sheridan Ross P.C.

(57) ABSTRACT

An optoacoustic sensor is configured to emit electromagnetic radiation and to detect acoustic waves, and a contact element is configured to be brought into contact with the object, the contact element being spaced from the optoacoustic sensor and being transparent to the electromagnetic radiation and the acoustic waves. Further, a scanning unit is configured to cause a movement of the optoacoustic sensor relative to the contact element, and a sealing element is configured to seal a space between the contact element and the optoacoustic sensor. The sealed space contains an acoustic coupling medium. At least a part of the sealing element is flexible to allow for the movement of the optoacoustic sensor relative to the contact element. Further, the optoacoustic sensor comprises a focused ultrasonic transducer configured to detect the acoustic waves generated in the object, the ultrasonic transducer having an axis of symmetry, (Continued)

and a light-emitting element configured to emit the electromagnetic radiation.

17 Claims, 5 Drawing Sheets

(58) Field of Classification Search
CPC .......... A61B 2562/146; A61B 2562/14; A61B 2562/164
See application file for complete search history.

(56) References Cited

U.S. PATENT DOCUMENTS

| | | | | |
|---|---|---|---|---|
| 2012/0150012 A1* | 6/2012 | Fujimoto | ............. | A61B 8/4281 600/407 |
| 2012/0296187 A1* | 11/2012 | Henning | ............ | A61B 5/14503 600/347 |
| 2015/0119683 A1* | 4/2015 | Kyono | ................ | A61B 5/0091 600/407 |
| 2015/0178959 A1* | 6/2015 | Huang | ................ | A61B 5/0095 600/407 |
| 2016/0058289 A1* | 3/2016 | Shigeta | ................ | A61B 8/4416 600/407 |
| 2016/0374565 A1* | 12/2016 | Nakajima | ............ | A61B 5/0095 600/323 |
| 2017/0115110 A1* | 4/2017 | Pelivanov | .......... | G01B 9/02097 |
| 2021/0298671 A1* | 9/2021 | Guder | ...................... | A61B 7/02 |

FOREIGN PATENT DOCUMENTS

| | | | | |
|---|---|---|---|---|
| EP | 2742853 A1 | * | 6/2014 | .......... A61B 5/0095 |
| JP | 2011-103913 | | 6/2011 | |
| JP | 2012127739 A | * | 7/2012 | |
| JP | 2013-165790 | | 8/2013 | |
| JP | 2016-013479 | | 1/2016 | |
| JP | 2016-101260 | | 6/2016 | |
| JP | 2016-101425 | | 6/2016 | |
| JP | 2017-006541 | | 1/2017 | |

OTHER PUBLICATIONS

English Summary of Official Action for Japan Patent Application No. 2019-160300, dated Apr. 3, 2023, 3 pages.

* cited by examiner

PROBE INCLUDING A SEAL WITH A PLEATED FLEXIBLE MEMBRANE FOR OPTOACOUSTIC IMAGING OF AN OBJECT, AND SYSTEM AND METHOD FOR THE SAME

CROSS-REFERENCE TO RELATED APPLICATION

This application claims the benefit of Europe Patent Application No. EP 18 192 394.7 filed Sep. 4, 2018, the entire contents of which are incorporated herein by reference.

FIELD OF THE INVENTION

The present invention relates to a probe, a system and a corresponding method for optoacoustic imaging of an object.

BACKGROUND OF THE INVENTION

Optoacoustic signal generation is based on the photoacoustic or optoacoustic effect, according to which ultrasonic waves are generated due to absorption of electromagnetic radiation by an object, e.g. a biological tissue, and a subsequent thermoelastic expansion of the object. Excitation radiation, for example non-ionizing laser light or radiofrequency radiation, can be pulsed radiation or continuous radiation with varying amplitude or frequency.

SUMMARY OF THE INVENTION

Because the absorption of electromagnetic radiation in tissue is usually a function of physiological properties, for example hemoglobin concentration or oxygen saturation, the optoacoustic effect is predestinated for utilization in medical imaging. In a possible approach, an optoacoustic sensor for irradiating the tissue with focused light and detecting the ultrasonic response is raster scanned across the surface of an object to obtain optoacoustic images with mesoscopic resolution. This approach is also referred to as raster-scanning optoacoustic mesoscopy (RSOM).

It is an object of the invention to improve optoacoustic imaging of an object, in particular to provide a probe and a system for optoacoustic imaging which allows for easy handling and deployment at various body parts and/or reliable imaging independent of the orientation of the probe.

This object is solved by the probe, the system and the method for optoacoustic imaging of object according to the independent claims.

The probe according to an aspect of the invention comprises an optoacoustic sensor configured to emit electromagnetic radiation and to detect acoustic waves generated in the object in response to irradiating the object with the electromagnetic radiation, and a contact element configured to be brought into contact with the object, the contact element being spaced from the optoacoustic sensor and being transparent to the electromagnetic radiation and the acoustic waves. Further, a scanning unit is configured to cause a movement of the optoacoustic sensor relative to the contact element along at least one lateral dimension of the contact element, and a sealing element is configured to seal a space between the contact element and the optoacoustic sensor. The sealed space between the contact element and the optoacoustic sensor contains an acoustic coupling medium for acoustically coupling the optoacoustic sensor to the contact element. At least a part of the sealing element is flexible to allow for the movement of the optoacoustic sensor relative to the contact element along the at least one lateral dimension of the contact element. Further, the optoacoustic sensor comprises a focused ultrasonic transducer configured to detect the acoustic waves generated in the object, the ultrasonic transducer having an axis of symmetry, and a light-emitting element configured to emit the electromagnetic radiation, wherein at least a part of the light-emitting element is located in the axis of symmetry of the ultrasonic transducer.

A contact element transparent to the electromagnetic radiation in the sense of the present invention may be optically non-diffusive (clear) or optically diffusive (translucent).

The system according to another aspect of the invention comprises a probe according to an aspect of the invention, a control unit configured to control the scanning unit to cause a movement of the optoacoustic sensor relative to the contact element along the at least one lateral dimension of the contact element, and a processing unit configured to generate optoacoustic images based on detection signals generated by the optoacoustic sensor upon detection of the acoustic waves.

The method according to yet another aspect of the invention comprises the following steps: controlling the scanning unit to move the optoacoustic sensor relative to the contact element along the at least one lateral dimension of the contact element to a plurality of positions; controlling the optoacoustic sensor to emit electromagnetic radiation while the optoacoustic sensor is being moved and/or located at the plurality of positions; controlling the optoacoustic sensor to detect acoustic waves generated in the object in response to irradiating the object with the electromagnetic radiation while the optoacoustic sensor is being moved and/or located at the plurality of positions and to generate according detection signals; and controlling the processing unit to generate at least one optoacoustic image based on the detection signals.

A preferred aspect of the invention is based on the approach of providing a, in particular handheld, probe having a sealed space which contains a coupling medium or can be filled with the coupling medium, wherein the sealed space is defined by a movable optoacoustic sensor or at least a part or section thereof, a preferably rigid or partially rigid contact element and a sealing element which seals the space between the optoacoustic sensor and the contact element. The sealing element is, at least partially, flexible such that the optoacoustic sensor can be moved relative to the contact element and/or an object which is contacted by the contact element. In other words, the optoacoustic sensor or at least a part thereof, the contact element and the at least partially flexible sealing element form a closed, deformable compartment, which adapts to and/or allows for the movement of the optoacoustic sensor relative to the contact element.

Further, the optoacoustic sensor comprises a, preferably single, focused ultrasonic transducer for detection of acoustic waves which are generated in the object in response to electromagnetic radiation emitted by a light-emitting element of the optoacoustic sensor. The transducer and the light-emitting element are arranged coaxially, in particular such that at least a part of the light-emitting element runs along an axis of symmetry of the transducer, resulting in a compact optoacoustic sensor. A combination of this compact sensor with the deformable compartment provides a probe for optoacoustic imaging with a smaller so-called footprint, i.e. a smaller interface between the probe and a surface of the object, compared to conventional probes.

Preferably, by means of the at least partially flexible sealing element the closed compartment is sealed in a fluid-tight, in particular liquid-tight and/or gas-tight, manner so that fluid, in particular liquid such as water and/or a coupling medium, enclosed in the compartment is safely retained in the compartment irrespective of the orientation of the probe, e.g. irrespective of whether the probe is placed on an object from above, below or the side.

Providing a sealed space containing the coupling medium is also advantageous compared to probes which use open tanks filled with coupling medium, because no time-consuming application of the open tank to the object and filling of the open tank with coupling medium is necessary Further, the sealed space allows to image the object at any angle, i.e. even if the interface between the probe surface of the object is oriented non-horizontally, in particular vertically. The inventive probe is thus suitable for flexible and fast deployment.

Preferably, the sealing element comprises a flexible membrane. The sealing element, in particular the flexible membrane, may span across the space between the optoacoustic sensor and the contact element, thereby sealing said space and forming a closed compartment. For example, the sealing element may form a dome above the contact element, wherein the optoacoustic sensor is located in the apex the dome, opposite to the contact element. Thus, the footprint of the probe is preferably defined only by the contact element.

Preferably, the sealing element may be pleated and/or have a shape similar to a sealing gaiter, gear gaiter, gearshift gaiter or bellows. In this way, the sealing element allows for a fluid-tight sealing of the space between the contact element and the optoacoustic sensor while ensuring a particularly reliable movement of the optoacoustic sensor relative to the contact element without obstruction or only a minimum of obstruction.

Locating at least a part of the light-emitting element in the axis of symmetry of the ultrasonic transducer provides emission of the electromagnetic radiation at the axis of symmetry of the transducer. Besides reducing the footprint of the probe, this allows to optimize the size of an illumination spot on the contact element, in particular a surface of the object contacted by the contact element, in which the electromagnetic radiation passes through the contact element or impinges on the object, respectively, with respect to a sensitivity field of the transducer. In particular, an illumination spot can be formed which substantially coincides with the diameter of a sensitivity field of the transducer at the surface such that only the volume in the sensitivity field is illuminated. Thus, the amount of electromagnetic energy deposited in the object for high quality optoacoustic imaging may be reduced compared to conventional illumination schemes.

Preferably, the light-emitting element is configured to emit divergent electromagnetic radiation, the emitted electromagnetic radiation forming an illumination cone which widens towards the contact element. By means of divergent illumination, an imaging depth of more than 1 mm, preferably more than 3 mm, in particular up to 5 mm, can be achieved. Also, divergent elimination can be achieved without gradient-index optics, e.g. so-called GRIN lenses, such that an even smaller footprint of the probe can be provided.

In summary, the invention allows for improved optoacoustic imaging of an object. In particular, the invention provides a probe which can be easily handled and deployed at various body parts and/or allows for reliable imaging independent of the orientation of the probe.

In a preferred embodiment, the probe further comprises a housing having a first housing portion enclosing the optoacoustic sensor and the sealing element, the first housing portion having a distal end and a proximal end, wherein the contact element is provided at the distal end of the first housing portion and/or forms the distal end of the first housing portion, and a second housing portion adjoining the proximal end of the first housing portion and having a lateral housing section extending along a lateral dimension of the contact element, the lateral housing section enclosing at least a part of the scanning unit. Preferably, the lateral housing section is dimensioned and/or shaped such that it can be held in or by the hand. In particular, the lateral housing section may have an elongate form and/or forms a handle of the probe. The lateral housing section may additionally comprise an anti-slip layer disposed on an outer surface of the second housing section for providing secure grip for an operator holding the probe in his hand. By these means, the probe becomes particularly comfortable or safe to use, respectively.

By providing a first and a second housing portion, the scanning unit, i.e. scanning stages, in particular stepper motors, may be spatially separated from the portion of the probe which comes into contact with the object, thereby providing a small footprint of the probe even in the case of a bulky scanning unit and allowing to obtain optoacoustic images even in spatially constricted areas of e.g. a human body.

Further, the second housing portion is preferably protruding beyond the first housing portion in the lateral dimension of the contact element, in particular such that the first housing portion enclosing the optoacoustic sensor forms a scan head of the probe. When operating the probe, this design allows for positioning the second housing portion away from the object while the first housing portion still comes into contact with the object. Thereby the footprint of the probe is determined solely by the size, in particular the diameter, of the first housing portion or the contact element arranged at the distal end of the first housing portion, respectively.

Preferably, the sealing element is arranged at the proximal end of the first housing portion which adjoins the second housing portion. In particular, the sealing element may be arranged to spatially separate the first housing portion from the second housing portion. For example, the sealing element can be configured to seal the second housing portion, in particular the lateral housing section, against the coupling medium contained in the space between the contact element and the optoacoustic sensor.

According to another preferred embodiment, the probe further comprises a coupling element configured to mechanically couple the optoacoustic sensor enclosed in the first housing portion to the scanning unit enclosed in the lateral housing section, thereby allowing a compact design of the first housing portion. Preferably, the coupling element is configured, e.g. formed, to provide a lateral offset between the optoacoustic sensor and the scanning unit. For instance, the coupling element may be configured as an angled coupling element and/or exhibit a step-like shape.

Alternatively or additionally, the coupling element comprises a recess configured to receive the optoacoustic sensor. The coupling element may further comprise one or more passages for receiving wiring for control of the optoacoustic sensor, in particular the focused ultrasonic transducer. In particular, the one or more passages can receive wiring to connect the focused ultrasound transducer with a control unit and/or a processing unit. By this means, the accommodation of the optoacoustic sensor and its wiring becomes particularly compact.

Alternatively or additionally, the coupling element comprises one or more passages for receiving at least part the light-emitting element and/or at least part of a light guide, a distal end of which may form the light-emitting element. Again, this allows for integrating the optoacoustic sensor and its optical connection into the housing in a particularly compact manner.

In yet another preferred embodiment, the movement exhibits an amplitude which is at least $1/15$, preferably at least $1/10$, more preferably at least $1/5$, in particular at least half of the dimension of the contact element along the at least one lateral dimension. In an exemplary embodiment, the movement has an amplitude between 2 and 15 mm, and the coupling element has a diameter of substantially 30 mm. By this means, a large portion, preferably substantially half of, the contact area in which the contact element contacts the object may be scanned by the optoacoustic sensor and thereby imaged. Thus, the available space in the housing of the probe, in particular the first housing portion, is efficiently used for movement of the optical sensor.

In yet another preferred embodiment, the movement exhibits an amplitude which corresponds to at least $1/4$ of the size, in particular the diameter, of the optoacoustic sensor along the at least one lateral dimension. In particular, the movement may exhibit an amplitude corresponding to at least half the size, in particular the diameter, of the focused ultrasonic transducer along the at least one lateral dimension. In an exemplary embodiment, the optoacoustic sensor has a diameter of substantially 30 mm, and the focused ultrasonic transducer has a diameter of 4 mm. A two-dimensional raster scan including movement along the at least one lateral dimension preferably covers a scanning area of at least 2 mm×2 mm, in particular 4 mm×2 mm. Providing accordingly large scanning amplitudes reduces the dead space in the housing, in particular the first housing portion.

In yet another preferred embodiment, the probe comprises a light guide having a proximal end and a distal end and configured to guide electromagnetic radiation coupled into the proximal end to the distal end of the light guide, the distal end of the light guide corresponding to or being coupled to the light-emitting element which is located in the axis of symmetry of the ultrasonic transducer. The light guide, for example an optical fiber, in particular a multimode fiber, provides a reliable and space-saving way for illuminating the object with electromagnetic radiation. In particular, the preferably flexible light guide can be easily integrated into the housing of the probe, in particular into passages of a coupling element which couples the optoacoustic sensor in the first housing portion to the scanning unit in the second housing portion. For example, the light guide may guide the electromagnetic radiation through the coupling element, in particular around the angle of the coupling element.

Further, a thin light guide, e.g. with a diameter of 500 μm or less, preferably 350 μm or less, in particular 250 μm or less, may be at least partially arranged at, in particular along, the axis of symmetry of the focused ultrasonic transducer without interfering with the detection capabilities of the transducer. Thereby, providing the emission of electromagnetic radiation in a center of the transducer may be achieved without inducing artifacts in the obtained optoacoustic images.

In yet another preferred embodiment, the light guide exhibits a numerical aperture larger than or equal to 0.3 and/or a core diameter smaller than 350 μm, preferably smaller than 250 μm. By this means, a divergent output beam of electromagnetic radiation is generated. Thus, an illumination spot on the contact element, in particular the surface of the object, much larger than the diameter of the light guide is provided. For example, an illumination spot with a diameter larger than 0.5 mm, preferably 1 mm, in particular 1.5 mm is achieved. This ensures gapless illumination in the sensitivity field of the focused ultrasonic detector, reducing image artifacts and/or enabling high signal-to-noise ratios.

In yet another preferred embodiment, the light guide comprises a coil section in which the light guide is coiled. By this means, particular large divergence of the electromagnetic radiation emitted by the light-emitting element can be achieved.

In particular, by bending the light guide in the coil section, mode hopping of the radiation guided by the light guide is induced, generating modes which exit the distal end of the light guide or the light-emitting element, respectively, at large exit angles corresponding with the high numerical aperture of the light guide.

In yet another preferred embodiment, the probe further comprises an illumination source configured to generate the electromagnetic radiation, and focusing optics configured to couple the electromagnetic radiation generated by the illumination source into the proximal end of the light guide, wherein the focusing optics comprises a numerical aperture of at least 0.25, in particular of at least 0.3. Preferably, the focusing optics comprises a numerical aperture substantially equal or at least comparable to the numerical aperture of the light guide. By this means, diverging electromagnetic radiation, in particular forming a radiation cone, can be reliably emitted by the optoacoustic sensor, in particular from the distal end of the light guide.

For example, the focusing optics may comprise a focusing lens having a short focal length, e.g. at most 10 cm, preferably at most 5 cm, in particular at most 1 cm.

In yet another preferred embodiment, the ultrasonic transducer comprises a central bore located in the axis of symmetry of the ultrasonic transducer, wherein the distal end of the light guide is located in the central bore. Preferably, the diameter of the bore is less than 10% of the diameter of the optoacoustic sensor, in particular of the focused ultrasonic transducer. For example, the bore has a diameter of 500 μm or less, preferably 350 μm or less, in particular 250 μm or less. By this means, coaxial illumination with divergent electromagnetic radiation emitted from the distal end of the light guide or the light-emitting element, respectively, at or at least close to a sensitive surface, in particular in the center thereof, of the focused ultrasonic transducer may be achieved, providing particularly efficient illumination.

In yet another preferred embodiment, the ultrasonic transducer is transparent to the electromagnetic radiation and is arranged between the distal end of the light guide and the contact element. By this means, the surface of the transducer sensitive to the acoustic waves is fully utilized, providing a particularly high signal-to-noise ratio.

In yet another preferred embodiment, the focused ultrasonic transducer comprises a sensitive surface, which is sensitive to acoustic waves. Preferably, the transducer further comprises an acoustic focal point, the distance of the acoustic focal point to the sensitive surface being larger than the distance between the sensitive surface and the contact element. Therefore, the acoustic focal point lies within the object when the contact element contacts the surface of the object. For example, the distance between the optoacoustic sensor, in particular the focused ultrasonic transducer, in particular the sensitive surface, to the contact element or the surface of the object, respectively, is 4 mm or less, preferably 3 mm or less, in particular 2.5 mm or less, and the distance between the focal point and the sensitive surface is between 3 mm and 5 mm, in particular substantially 4 mm. By this means, a particularly high imaging depth can be achieved.

In yet another preferred embodiment, the processing unit is configured to generate the optoacoustic image using a weighted back-projection of the detection signals, taking into account a sensitivity field of the optoacoustic sensor, in particular of the single focused ultrasonic transducer. Preferably, the processing unit is configured to apply a reconstruction algorithm for reconstruction of the optoacoustic image which models the reconstruction through the acoustic focal point of the transducer. By this means, high image quality with high resolution and reduced image artifacts can be achieved.

Preferably, the weighted back-projection comprises a term which is a combination of a direct term and a derivative term with an additional weighting factor corresponding to the sensitivity field of the transducer. For example, the weighted back-projection can be expressed by $$\Delta p_0(\vec{r}) = \Sigma_{i=1}^N W_i(\vec{r}) \cdot b(\vec{r}_i, NN(t_{sp,j}; |\vec{r}-\vec{r}_i|))$$  1.

wherein $W_i(\vec{r})$ is a weight defined by the sensitivity field, $b(t_{sp})$ is the back-projection term and NN(t; R) corresponds to the nearest neighbor. The back-projection term may be given by $$b(t_{sp}) = \left[ b \cdot p(t_{sp}) - t_{sp} \frac{\partial p(t_{sp})}{\partial t_{sp}} \right]_{t_{sp}=|\vec{r}-\vec{r}_i|}$$  2.

wherein $p(t_{sp})$ is a recorded A-line and b=10 is a parameter compensating for the acceptance angle of the transducer.

In yet another preferred embodiment, the control unit is configured to position an acoustic focus point of the optoacoustic sensor at an acoustic focus point depth which is substantially in the middle of an imaging depth range from which acoustic waves are detected for generation of the optoacoustic images. For example, for an imaging depth between 1.5 mm and 2 mm, the acoustic focus point may be positioned at an acoustic focus point depth between 0.75 and 1 mm. By this means, the diameter of the illumination spot on the contact element or the surface of the object, respectively, may be adapted to the diameter of the sensitivity field at the contact element or surface, respectively, and reduced by a factor of 4 or larger compared to conventional illumination schemes. Thereby, particularly efficient illumination is provided.

In particular, the control unit is configured to position the acoustic focus point of the acoustic sensor at an acoustic focus point depth such that the diameter of the illumination spot generated by the electromagnetic radiation emitted by the optoacoustic sensor is between 90 and 200%, preferably between 100 and 150%, of the lateral width of the sensitivity field of the optoacoustic sensor at the imaging depth. By this means, a reliable and homogeneous illumination of absorbers generating the acoustic waves in the object inside the sensitivity field of the optoacoustic sensor is provided.

In yet another preferred embodiment, the system further comprises an alignment assembly configured for attachment to a surface of the object, the alignment assembly having a docking element, in particular a recess, configured to receive the contact element of the probe. By means of the alignment assembly, the probe, in particular the first housing portion, may be precisely positioned on the surface of the object.

In yet another embodiment, the alignment assembly comprises a contact surface configured to be brought into contact with the object, the contact surface having glue and/or a high friction material disposed thereon. By this means, the alignment assembly is secured to the surface and unwanted motion of the probe along the surface of the object during imaging of the object may be prevented or at least reduced.

In yet another embodiment, the system further comprises a holding element configured to hold and/or position the probe relative to the object, in particular relative to the alignment assembly, preferably in a coupling position in which the probe is received by the alignment assembly. Preferably, the lateral housing section of the first housing portion of the housing of the probe is dimensioned and/or shaped such that it can be held by the holding element. In particular, the lateral housing section can be configured for attachment to the holding element. The holding element, in particular in interaction with the alignment assembly, allows to position the probe with particularly high precision.

Preferably, the holding element is designed as a robot arm or hand, and configured to automatically position the probe relative to the object. Preferably, both the holding element and the probe further comprises a dedicated interface configured for coupling the optoacoustic sensor, in particular the focused ultrasonic transducer and/or the light-emitting element, and/or the scanning unit to the holding element, in particular the robot arm or hand.

BRIEF DESCRIPTION OF THE DRAWINGS

Further advantages, features and examples of the present invention will be apparent from the following description of following figures.

DETAILED DESCRIPTION

Figure 1:
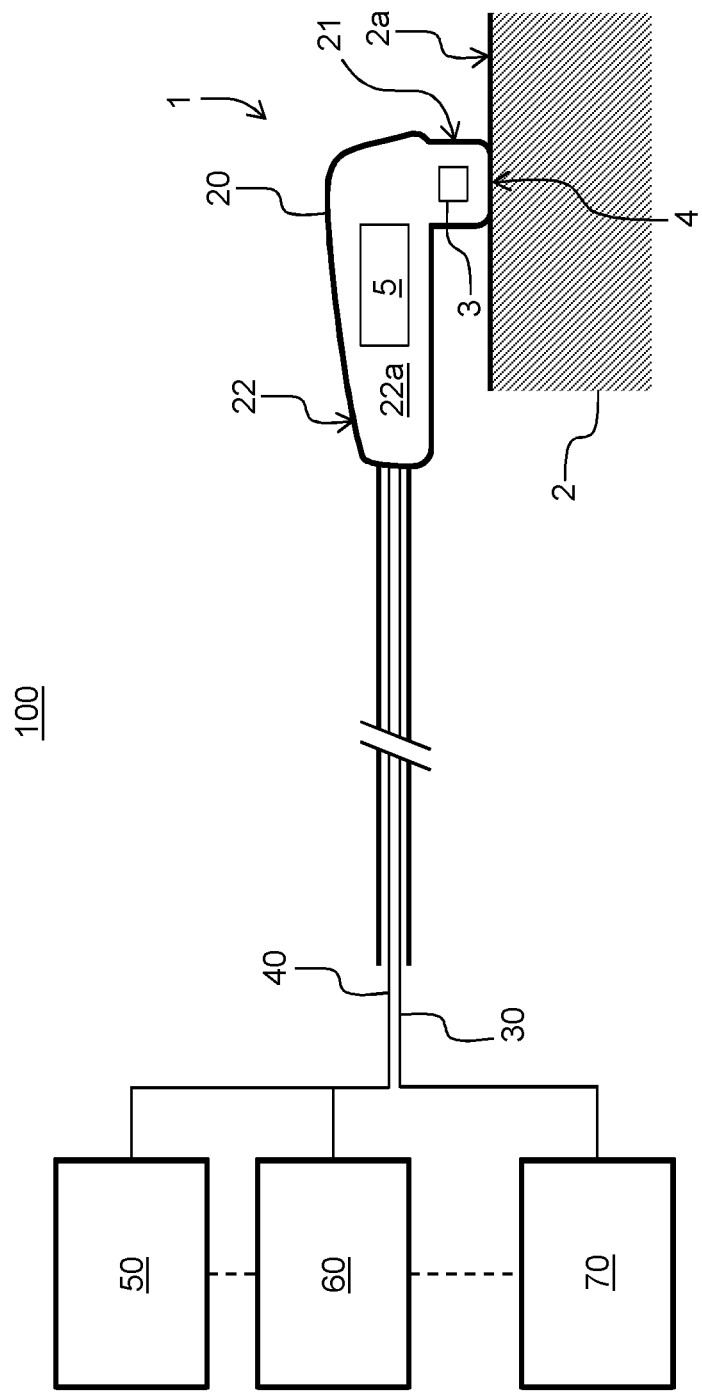
FIG. 1 shows an example of a system for optoacoustic imaging of an object.

FIG. 1 shows an example of a system 100 for optoacoustic imaging of an object 2 in a schematic representation. The system 100 comprises a probe 1 for contacting the object 2 at the surface 2a of the object 2, the probe 1 having an optoacoustic sensor 3 for irradiating the object 2 with electromagnetic radiation and detecting acoustic waves generated in the object 2 in response thereto. The system 100 further comprises a control unit 50, a processing unit 60 and an illumination source 70, the control unit 50, the processing unit 60 and the source 70 being coupled to the probe 1, in particular to the optoacoustic sensor 3, via wiring 40 or a light guide 30, respectively.

The control unit 50 is configured to control a scanning unit 5 of the probe 1 to cause a movement of the optoacoustic sensor 3 relative to an acoustically and optically transparent contact element 4 of the probe 1 which contacts the object 2 upon imaging. In particular, the control unit 50 is configured to control the scanning unit 5 such that the optoacoustic sensor 3 is raster scanned across the surface 2a of the object 2. Further, the control unit 50 is configured to control the scanning unit 5 to adjust the distance between the optoacoustic sensor 3 and the contact element 4 or the surface 2a of the object 2 in order to adjust an imaging depth.

The processing unit 60 is configured to generate optoacoustic images based on detection signals generated by the optoacoustic sensor 3 upon detection of the acoustic waves. For example, the processing unit 60 is configured to perform a weighted back-projection of the detection signals in order to model the reconstruction of an optoacoustic image through an acoustic focal point of the optoacoustic sensor 3.

The illumination source 70, e.g. a laser, is configured to generate the electromagnetic radiation which is provided at the optoacoustic sensor 3 via the light guide 30.

The control unit 50, the processing unit 60 and the illumination source 70 may be communicatively interconnected for coordinating the optoacoustic imaging, the interconnection being indicated by the dotted lines.

For example, the control unit 50 may be configured to control the scanning unit 5 to move the optoacoustic sensor 3 relative to the contact element 4 along at least one lateral dimension of the contact element 4, in particular along the surface 2a of the object 2, to a plurality of positions. The control unit 50 further controls the source 70 to generate the electromagnetic radiation while the optoacoustic sensor 3 is being moved and/or located at the plurality of positions. Also, the control unit 50 controls the processing unit 60 to process the detection signals generated by the optoacoustic sensor 3 in response of the detection of acoustic waves generated in the object 2, such that an optoacoustic image is generated.

The probe 1 comprises a housing 20 which encloses the optoacoustic sensor 3 and the scanning unit 5. The housing 20 is configured to be grasped by an operator with his hand. In particular, the housing 20 is shaped so that it can be held in or by a hand of the operator. To this end, the housing 20 comprises a first housing portion 21 which encloses the optoacoustic sensor 3, and a second housing portion 22 which encloses the scanning unit 5, the second housing portion 22 having a lateral housing section 22a which extends parallel to a lateral dimension of the contact element 4. In particular, the lateral housing section 22a protrudes beyond the first housing section 21 in a direction parallel to the contact element 4, i.e. parallel to the surface 2a of the object 2. The lateral housing section 22a has an elongate form which is particularly suited to be grasped by the hand of the operator. In other words, the second housing portion 22, in particular the lateral housing section 22a, forms a handle of the probe 1.

Figure 2:
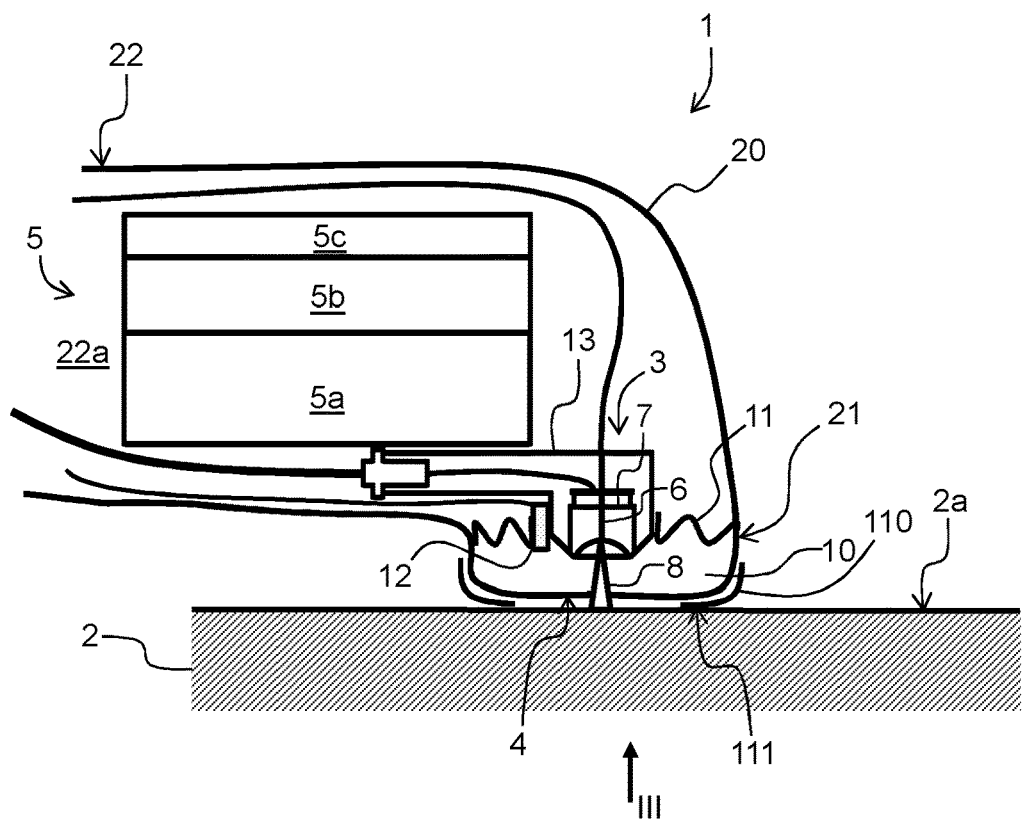
FIG. 2 shows an example of a probe for optoacoustic imaging of an object in a side view.

FIG. 2 shows a schematic representation of an example of a probe 1 for optoacoustic imaging of an object 2 in a side view. The probe 1 comprises a housing 20 enclosing an optoacoustic sensor arranged in a, preferably rigid, first housing portion 21, and a scanning unit 5 configured to cause a movement of the optoacoustic sensor 3 and arranged in a, preferably rigid, second housing portion 22. A light-emitting element 6 of the optoacoustic sensor 3 is configured to emit electromagnetic radiation 8, and a focused ultrasonic transducer 7 of the optoacoustic sensor 3 is configured to detect acoustic waves generated in the object 2 in response to irradiating the object 2 with the electromagnetic radiation 8.

The probe 1 further comprises a, preferably rigid or partially rigid, contact element 4 configured to be brought into contact with the object 2, in particular with the surface 2a of the object 2, wherein the contact element 4 is arranged opposite of the optoacoustic sensor 3.

Preferably, the first housing portion 21 has a distal end section facing the object 2 and/or contacting the object 2 when the probe 1 is in use, i.e. the probe 1 is used to acquire optoacoustic images from the object 1.

Preferably, the contact element 4 forms a part of the, preferably distal end section of the, first housing portion 21 and/or is integrated into a section, preferably into the distal end section, of the first housing portion 21.

Preferably, the contact element 4 comprises a rigid frame or rigid edge structure and a flexible and transparent membrane which is stretched across the frame or edge structure, respectively. As a result, the contact element 4 has a rigid outer area and a central area, which is—at least to some extent—mechanically flexible.

The space 10 between the contact element 4 and the optoacoustic sensor 3 is sealed by a sealing element 11 such that a coupling medium for acoustically coupling the contact element 4 with the optoacoustic sensor 3 can be contained in the space 10. The sealing element 11 is at least partially flexible such that it allows for movement of the optoacoustic sensor 3 relative to the contact element 4.

Preferably, the sealing element 11 may have a shape corresponding to or similarly to a sealing gaiter, gear gaiter or gearshift gaiter to allow for, on the one hand, a fluid-tight sealing of the space 10 between the contact element 4 and the optoacoustic sensor 3 and, on the other hand, a particularly reliable movement of the optoacoustic sensor 3 relative to the contact element 4 with no obstruction or only a minimum of obstruction.

The probe 1 may also comprise an optical imaging device 12, e.g. a camera, which can be part of the optoacoustic sensor 3 or arranged adjacent to the optoacoustic sensor 3 such that a field of view of the optical imaging device 12 substantially corresponds with the contact element 4.

Figure 3:
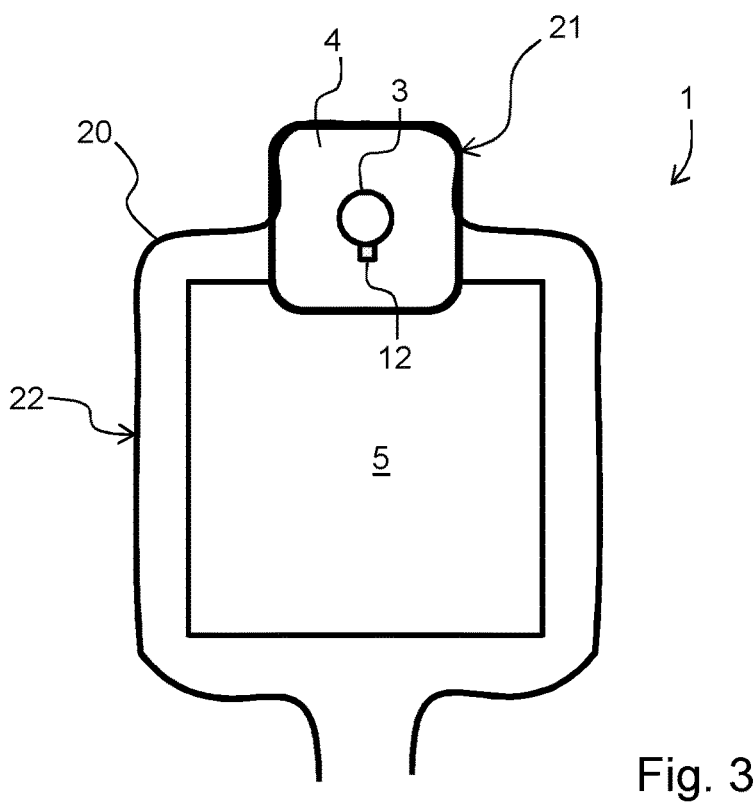
FIG. 3 shows the probe of FIG. 2 in a bottom view.

The scanning unit 5 comprises three scanning stages 5a, 5b, 5c, e.g. stepper motors, for moving the optoacoustic sensor 3 independently along three dimensions perpendicular to each other, including two lateral dimensions and one transversal dimension. The optoacoustic sensor 3 is coupled to the scanning unit 5, in particular at least one scanning stage 5a of the three scanning stages 5a, 5b, 5c, by means of a coupling element 13. The coupling element 13 is designed such that the scanning unit 5 in the second housing portion 22 is spatially separated from the optoacoustic sensor 3 in the first housing portion 21. In particular, the coupling element 13 may be designed as an angled coupling element 13 such that the optoacoustic sensor 3 exhibits a lateral offset with respect to the scanning unit 5 along a lateral dimension of the contact element 4. Thus, the bulky scanning unit 5 can be arranged in a lateral housing section 22a of the second housing portion 22 which protrudes beyond the first housing portion 21. Thereby, the first housing portion 21 defines the compact scan head of the probe 1 with a small footprint, as also shown in FIG. 3 discussed below.

On the surface 2a of the object 2 an alignment assembly 110 may be provided which is configured to couple the probe 1 to the surface 2a of the object 2. For example, the alignment assembly 110 may be ring-like and comprises a recess for at least partially receiving the probe 1, in particular the first housing section 21, at least the contact element 4. The alignment assembly 110 further comprises an imaging window, e.g. a central hole, which preferably substantially corresponds to the size, in particular the diameter, of the contact element 4, and through which the electromagnetic radiation and the acoustic waves passes.

The alignment assembly 110 preferably comprises a contact surface 111 for securely attaching, e.g. gluing, the alignment assembly 110 to the surface 2a of the object 2. An operator, for example a physician, may mark a region on the surface 2a of the object 2, e.g. a human body, by attaching the alignment assembly 110 to the surface 2a and subsequently perform optoacoustic imaging in the marked region by docking the probe 1 to the alignment assembly 110, i.e. inserting at least part of the first housing portion 21 into the recess of the alignment assembly 110.

In the example shown in FIG. 2, the contact element 4 is spaced from the surface 2a of the object 2 and an inner surface of the alignment assembly 110 for illustration purposes. In use, however, it is preferred that the contact element 4 is closer to or, at least partially, in contact with the surface 2a of the object 2 and the inner surface of the alignment assembly 110 to ensure a particularly good acoustic and/or optical coupling between the object 2 and the coupling element 2 and/or optoacoustic sensor 3 or, respectively, secure fit of the distal end of the probe 1 in the recess of the alignment assembly 110.

FIG. 3 shows the probe 1 of FIG. 2 in a bottom view, i.e. from a perspective indicated by the arrow III in FIG. 2. The second housing portion 22 of the housing 20 protrudes laterally beyond the first housing portion 21. Therefore, the scanning unit 5 is laterally positioned in an off-set manner with respect to the optoacoustic sensor 3 and the optical imaging device 12.

As during regular operation of the probe 1 only the contact element 4 contacts the object 2, the footprint of the probe 1 is defined substantially only by the first housing portion 21, in particular the contact element 4. The probe 1 may therefore be employed to optoacoustically image objects in regions with winding surfaces where it is essential, for a reliable contact between the contact element 4 and the surface of the object, that the footprint of the probe 1 is as small as possible.

Figure 4:
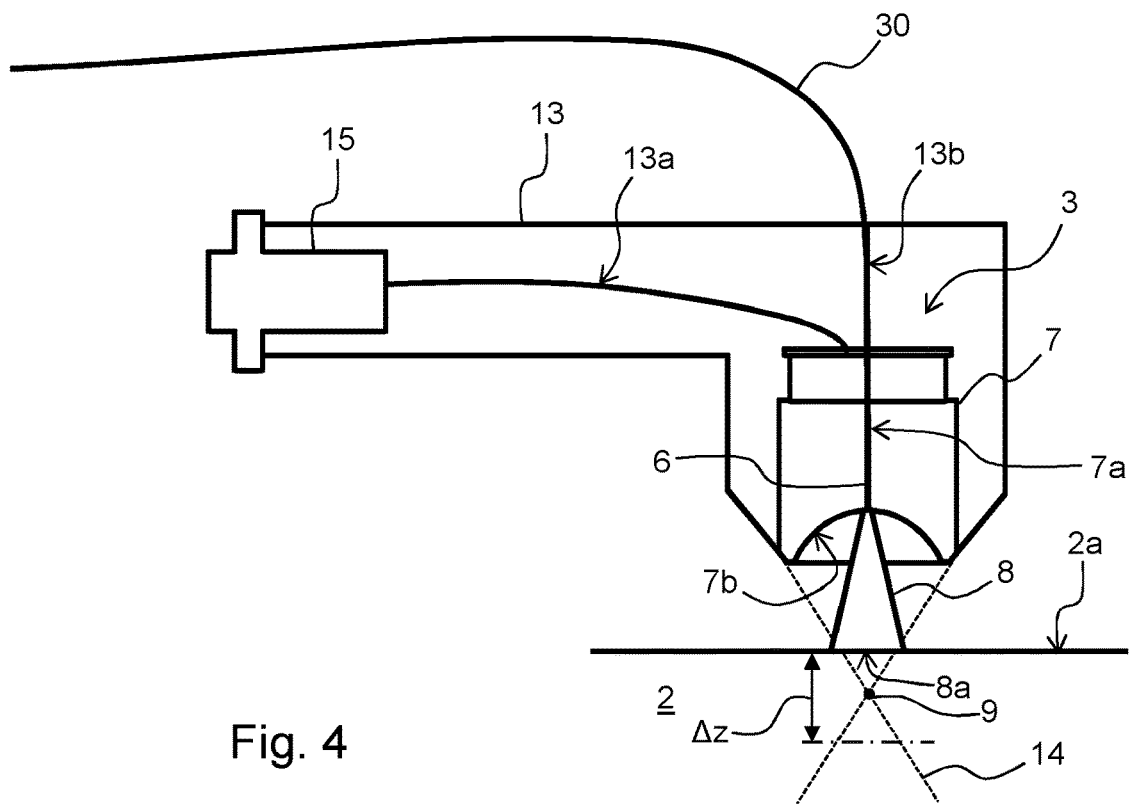
FIG. 4 shows an example of an optoacoustic sensor with a light-emitting element and a focused ultrasonic transducer wherein the light-emitting element is located in a central bore of the focused ultrasonic transducer.

FIG. 4 shows an example of an optoacoustic sensor 3 in a schematic representation. The optoacoustic sensor 3 comprises a light-emitting element 6 configured to emit electromagnetic radiation 8 and a focused ultrasonic transducer 7 configured to detect acoustic waves generated in response to irradiating an object 2 with the electromagnetic radiation 8. The focused ultrasonic transducer 7 has a central bore 7a running along an axis of symmetry of the optoacoustic sensor 3 or the focused ultrasonic transducer 7, respectively, in which the light-emitting element 6 is located.

The optoacoustic sensor 3 is integrated into a coupling element 13, in particular located in a recess of the coupling element 13. The coupling element 13 comprises passages 13a, 13b configured to receive wiring for control of the focused ultrasonic transducer 7, in particular for transmission of detection signals generated by the focused ultrasonic transducer 7 upon detection of acoustic waves, or a portion of a light guide 30 for coupling the light-emitting element 6 to an external illumination source (see FIG. 1). The wiring for control of the focused ultrasonic detector 7 couples the focused ultrasonic transducer 7 to a sensor interface 15 configured for connection with a control unit and/or a processing unit via further wiring (see FIG. 1).

A distal end of the light guide 30 is inserted into the central bore 7a and forms the light-emitting element 6. Thus, electromagnetic radiation 8 guided by the light guide 30 to the optoacoustic sensor 3 exits the distal end of the light guide 30 in the center of the focused ultrasonic transducer 7 and propagates towards the object 2 in a divergent manner, forming an illumination spot 8a on a surface 2a of the object 2.

Preferably, the focused ultrasonic transducer 7 is a spherically focused ultrasonic transducer comprising a curved sensitive surface 7b which is sensitive to the acoustic waves. In order to allow reliable high-resolution optoacoustic imaging with high signal to noise ratio in human tissue, for example of the human vasculature throughout the whole skin depth, i.e. up to an imaging depth of 5 mm, a center frequency of the transducer 7 preferably lies above 40 MHz, in particular at substantially 50 MHz, and a detection bandwidth of the transducer 7 preferably lies above 90 MHz at −6 db, in particular above 100 MHz at −6 db.

A sensitivity field 14 of such a transducer 7 preferably exhibits a substantially double cone shape. An acoustic focus point 9 of the transducer 7 lies at the apex of the double cone-shaped sensitivity field 14. For imaging an object, the sensitive surface 7b is preferably positioned in a distance from the surface 2a of the object 2 such that the acoustic focus point 9 lies inside the object 2. Further preferably, the light-emitting element 6 or the distal end of the light guide 30, respectively, is configured to emit the electromagnetic radiation 8 in a manner that the illumination spot 8a on the surface 2a of the object 2 is at least as large as the diameter the of the sensitivity field 14 at the surface 2a. By this means, sufficient electromagnetic radiation to generate strong optoacoustic signals can be provided in an imaging depth $\Delta z$ below the surface 2a, in particular in a depth twice as deep in the object 2 as the acoustic focus point 9.

Figure 5:
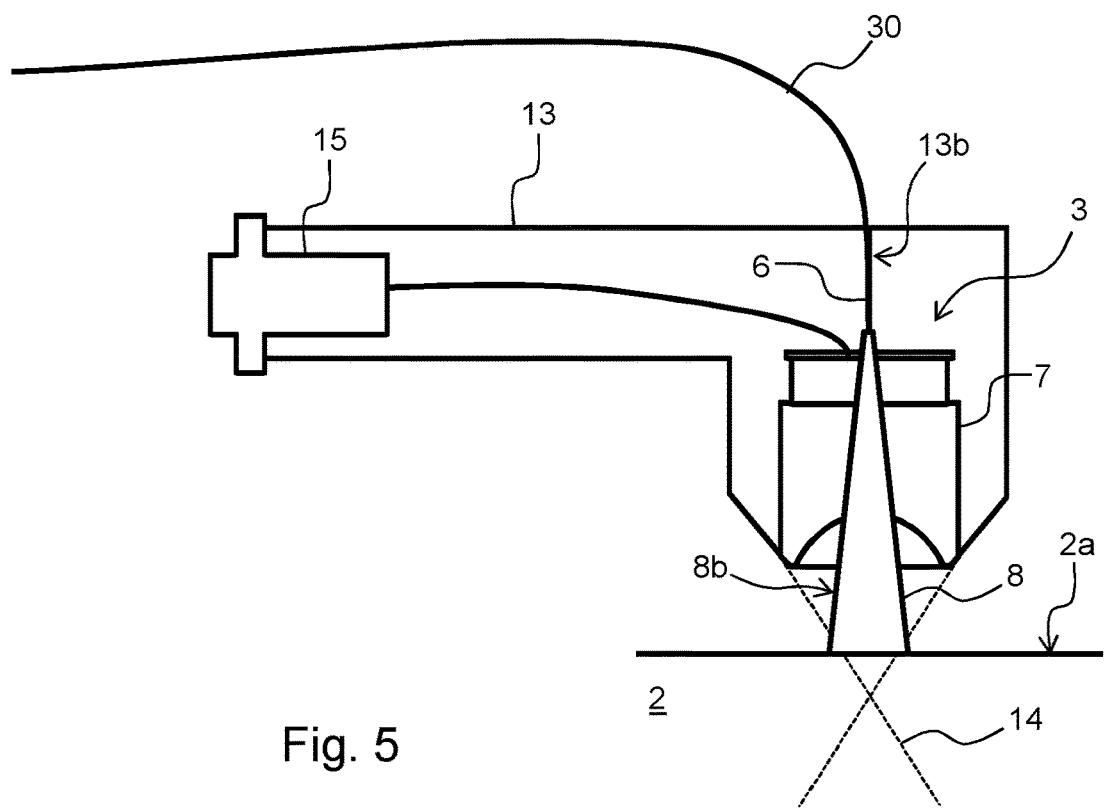
FIG. 5 shows an example of an optoacoustic sensor with a light-emitting element and a focused ultrasonic transducer wherein the focused ultrasonic transducer is transparent for electromagnetic radiation emitted by the light-emitting element.

FIG. 5 shows an example of an optoacoustic sensor 3 with a light-emitting element 6 and a focused ultrasonic transducer 7, wherein the focused ultrasonic transducer 7 is transparent for electromagnetic radiation 8 emitted by the light-emitting element 6. Similar to FIG. 4, the light-emitting element 6 is formed by the distal end of a light guide 30 configured to guide electromagnetic radiation, e.g. from an external illumination source, to the optoacoustic sensor 3. In this embodiment, the optoacoustic sensor 3 is located between the distal end of the light guide 30 and a contact element (see FIG. 2) which is configured to contact the surface 2a of an object 2.

The optoacoustic sensor 3 is located in a recess of a coupling element 13 and the distal end of the light guide 10 is received by a passage 13b of the coupling element 13. The recess and the passage 13b are arranged coaxially such that the distal end of the light guide 30 is located in an axis of symmetry of the focused ultrasonic transducer 7. By this means, an illumination cone 8b adapted to a, in particular double cone-shaped, sensitivity field 14 of the transducer 7 may be generated.

Figure 6:
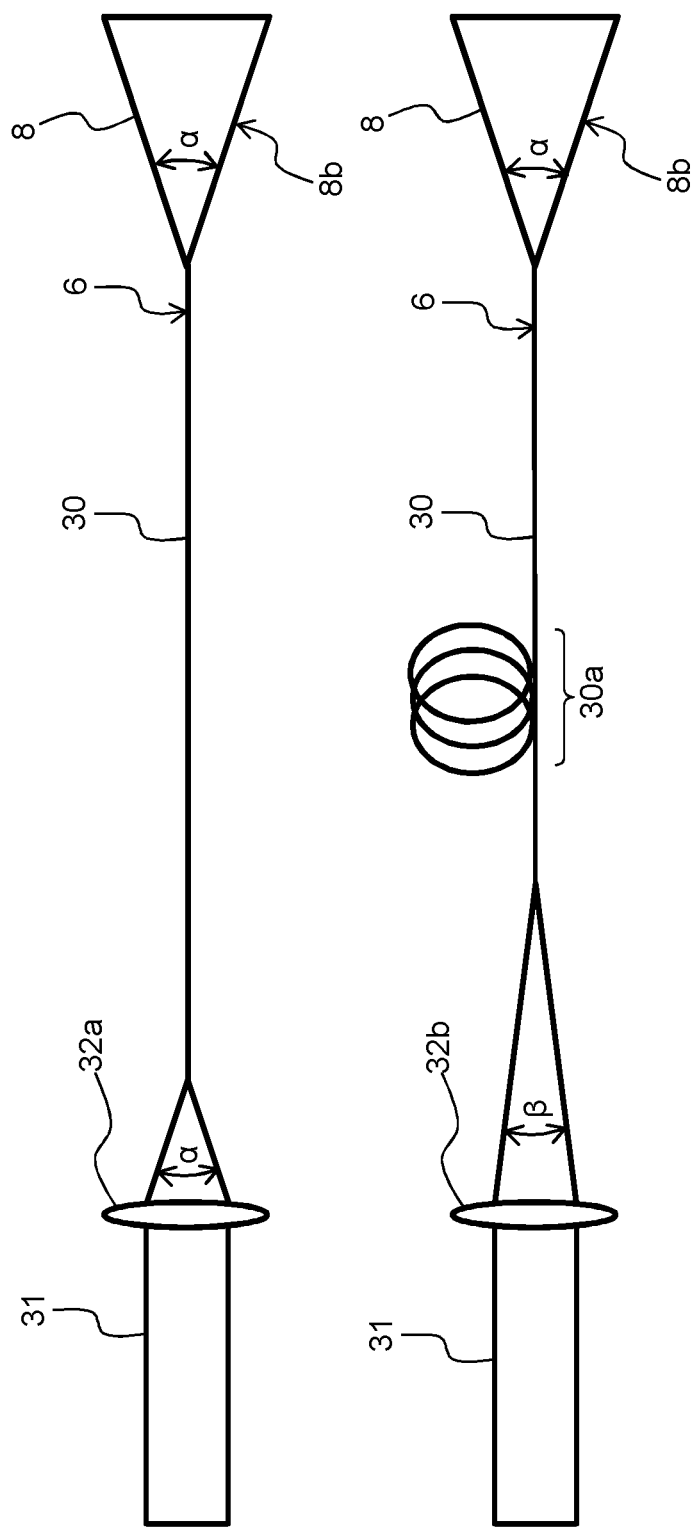
FIG. 6 shows examples for a light guide emitting divergent electromagnetic radiation at a distal end forming a light-emitting element.

FIG. 6 shows examples for a light guide 30 emitting divergent electromagnetic radiation 8, in particular in form of an illumination cone 8b, at a distal end forming a light-emitting element 6. In order to enable the divergence of the electromagnetic radiation 8, in particular the illumination cone 8b, at the distal end, the light guide 30 may be composed of a, in particular multimode, optical fiber with high numerical aperture, in particular with a numerical aperture more than 0.2, preferably more than 0.25, for example more than or equal to 0.3, and/or a core diameter of less than 350 µm, preferably less than 250 µm, for example substantially 200 µm.

To generate the divergence of the electromagnetic radiation 8, in particular the illumination cone 8b, at the distal end, the coupling of electromagnetic radiation 8 into the light guide 30 at a proximal end opposite to the distal end forming the light-emitting element 6 is performed using focusing optics with a high numerical aperture, in particular an numerical aperture comparable to the numerical aperture of the light guide 30 as shown in FIG. 6A. For example, a collimated beam 31 of electromagnetic radiation 8 is focused with a focusing lens 32a having a short focal length onto the proximal end of the light guide 30 such that an entrance angle α of the electromagnetic radiation 8 at the proximal end corresponds to an exit angle α of the electromagnetic radiation 8 at the distal end.

Alternatively or additionally, the electromagnetic radiation 8 is coupled into the proximal end of the light guide 30 with focusing optics having a low numerical aperture, in particular lower than the numerical aperture of the light guide 30. The light guide comprises a coil section 30a in which the light guide 30 is coiled, thereby inducing mode hoping towards modes of the electromagnetic radiation 8 which exit the light guide 30 at the distal end with an angle determined by the numerical aperture of the light guide 30. For example, the collimated beam 31 of electromagnetic radiation 8 is focused with the focusing lens 32b having a large focal length on to the proximal end of the light guide 30 with an entrance angle β. By manipulating the modes of the electromagnetic radiation 8 guided by the light guide 30 by means of bending the light guide 30, the electromagnetic radiation 8 is emitted at the distal end with an exit angle α larger than the entrance angle β, in particular with an exit angle determined by the numerical aperture of the light guide 30.

Figure 7:
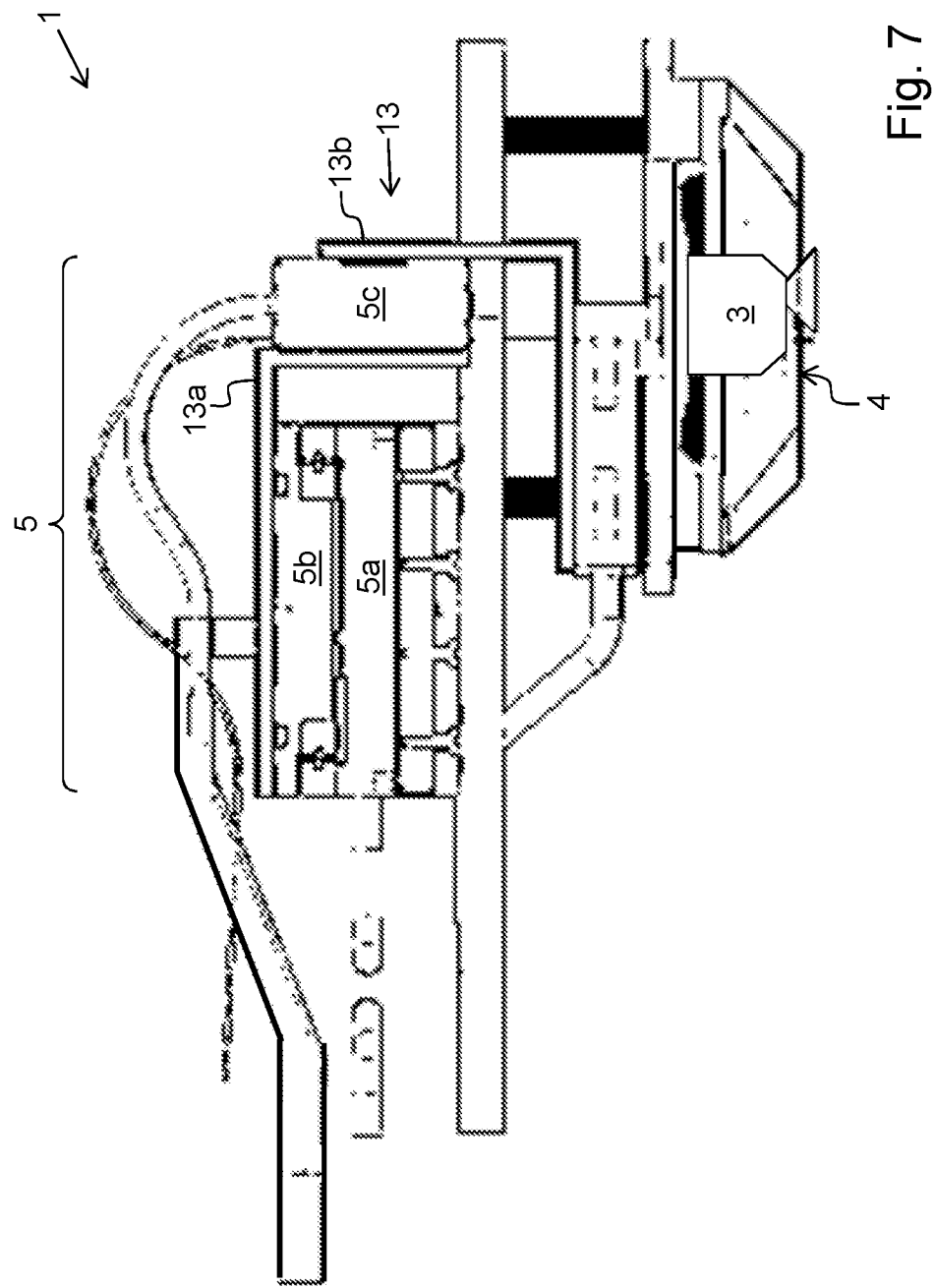
FIG. 7 shows an exemplary arrangement of a scanning unit of a probe for optoacoustic imaging in a side view.

FIG. 7 shows an exemplary arrangement of a scanning unit 5 of a probe 1 for optoacoustic imaging in a side view. The scanning unit 5 comprises three scanning stages 5a, 5b, 5c configured to move an optoacoustic sensor 3 of the probe 1 relative to a contact element 4, wherein the contact element 4 is configured to be brought into contact with an object for optoacoustic imaging. A mechanical coupling between the scanning unit 5 and the optoacoustic sensor 3 is provided by a coupling element 13.

In the present example, the coupling element 13 provides a lateral offset between the scanning unit 5 and the optoacoustic sensor 3 allowing for a more compact housing of the probe 1 (see FIG. 2). The coupling element 13 particularly allows arrangement of the scanning unit 5 in a second housing portion adjoining a first housing portion, wherein only the first housing portion, or components thereof, respectively, come into contact with an object to be optoacoustically imaged.

To further improve the shape of the housing, in particular the second housing portion, e.g. to provide more ergonomic handling of the probe 1, a first and a second of the scanning stages 5a, 5b are arranged adjacent to each other, e.g. on top of each other, whereas a third of the scanning stages 5c is arranged apart from the two scanning stages 5a, 5b. In particular, the third scanning stage 5c is positioned laterally with regard to the first and second scanning stage 5a, 5b, e.g. in front of the first and second scanning stage 5a, 5b. By this means, a further lateral offset is provided between the scanning unit 5 and the optoacoustic sensor 3.

In this arrangement, the first and second scanning stage 5a, 5b may be mechanically coupled to the third scanning stage 5c by means of a first coupling portion 13a of the coupling element 13, whereas the third scanning stage 5c may be mechanically coupled to the optoacoustic sensor 3 by means of a second coupling portion 13b of the coupling element 13. Preferably, the third scanning stage 5c is configured to move the optoacoustic sensor 3 perpendicular to the contact element 4, whereas the first or second scanning stage 5a, 5b is configured to move the optoacoustic sensor 3 along a lateral dimension, i.e. parallel to the contact element 4, respectively.

What is claimed is:

1. A probe for optoacoustic imaging of an object, comprising:
    an optoacoustic sensor configured to emit electromagnetic radiation and to detect acoustic waves generated in the object in response to irradiating the object with the electromagnetic radiation;
    a contact element configured to be brought close to or into contact with the object, the contact element being spaced from the optoacoustic sensor and being transparent to the electromagnetic radiation and the acoustic waves;
    a scanner configured to cause a movement of the optoacoustic sensor relative to the contact element along at least one lateral dimension of the contact element; and
    a seal configured to create a sealed space between the contact element and the optoacoustic sensor, the sealed space between the contact element and the optoacoustic sensor containing an acoustic coupling medium for acoustically coupling the optoacoustic sensor to the contact element, and at least a part of the seal being flexible to allow for the movement of the optoacoustic sensor relative to the contact element along the at least one lateral dimension of the contact element;
    wherein the optoacoustic sensor comprises
        a focused ultrasonic transducer configured to detect the acoustic waves generated in the object, the ultrasonic transducer having an axis of symmetry;
        a light-emitting element configured to emit the electromagnetic radiation, wherein at least a part of the light-emitting element is located in the axis of symmetry of the ultrasonic transducer; and
    wherein the seal comprises a flexible membrane spanning across the space between the optoacoustic sensor and the contact element, thereby sealing said space so that the optoacoustic sensor or at least a part of the optoacoustic sensor, the contact element, and the flexible membrane of the seal form a closed deformable compartment that adapts to the movement of the optoacoustic sensor relative to the contact element along the at least one lateral dimension of the contact element, wherein the flexible membrane of the seal is pleated and has a shape of a sealing gaiter that allows for a fluid-tight sealing of the space between the contact element and the optoacoustic sensor and that allows for the movement of the optoacoustic sensor relative to the contact element along the at least one lateral dimension of the contact element.

2. The probe according to claim 1, the scanner comprising at least one scanning stage configured to move the optoacoustic sensor relative to the contact element along at least one lateral dimension of the contact element, and the probe further comprising a housing having:
- a first housing portion enclosing the optoacoustic sensor and the seal, the first housing portion having a distal end and a proximal end, wherein the contact element is provided at the distal end of the first housing portion; and
- a second housing portion adjoining the proximal end of the first housing portion and having a lateral housing section extending along a lateral dimension of the contact element, the lateral housing section enclosing at least a part of the at least one scanning stage, so that the optoacoustic sensor, which is enclosed in the first housing portion, exhibits, along the lateral dimension of the contact element, a lateral offset with respect to the at least one scanning stage, which is at least partially enclosed in the lateral housing section of the second housing portion;
- wherein the lateral housing section is preferably dimensioned and shaped such that it can be held in or by the hand.

3. The probe according to claim 1, comprising a light guide having a proximal end and a distal end and configured to guide electromagnetic radiation coupled into the proximal end to the distal end of the light guide, the distal end of the light guide corresponding to or being coupled to the light-emitting element which is located in the axis of symmetry of the ultrasonic transducer.

4. The probe according to claim 3, wherein the light guide exhibits a numerical aperture larger than or equal to 0.3.

5. The probe according to claim 3, the light guide comprising a coil section in which the light guide is coiled.

6. The probe according to claim 3, further comprising:
- an illumination source configured to generate the electromagnetic radiation, and
- focusing optics configured to couple the electromagnetic radiation generated by the illumination source into the proximal end of the light guide, wherein the focusing optics comprise a numerical aperture of at least 0.25, preferably of at least 0.3.

7. The probe according to claim 3, the ultrasonic transducer comprising a central bore located in the axis of symmetry of the ultrasonic transducer, wherein the distal end of the light guide is located in the central bore.

8. The probe according to claim 1, the ultrasonic transducer being transparent to the electromagnetic radiation and being arranged between the distal end of the light guide and the contact element.

9. The probe according to claim 1, the focused ultrasonic transducer comprising a sensitive surface, which is sensitive to acoustic waves, and an acoustic focal point, the distance of the acoustic focal point to the sensitive surface being larger than the distance between the sensitive surface and the contact element.

10. A system for optoacoustic imaging of an object, comprising:
- a probe according to claim 1,
- a controller configured to control the scanner to cause a movement of the optoacoustic sensor relative to the contact element along the at least one lateral dimension of the contact element, and
- a processor configured to generate optoacoustic images based on detection signals generated by the optoacoustic sensor upon detection of the acoustic waves.

11. The system according to claim 10, wherein the processor is configured to generate the optoacoustic image using a weighted back-projection of the detection signals, taking into account a sensitivity field of the optoacoustic sensor, in particular of the single focused ultrasonic transducer.

12. The system according to claim 10, wherein the controller is configured to position an acoustic focus point of the optoacoustic sensor at an acoustic focus point depth which is within an imaging depth range ($\Delta z$) from which acoustic waves are detected for generation of the optoacoustic images.

13. The system according to claim 10, further comprising an alignment assembly configured for being attached to a surface of the object, the alignment assembly having a contact surface configured to be brought into contact with the object, an alignment body, and a docking element, in particular a recess, configured to receive the contact element of the probe.

14. The system according to claim 13, wherein the contact surface has glue disposed thereon.

15. A method for controlling a system according to claim 10, the method comprising:
- controlling the scanner to move the optoacoustic sensor relative to the contact element along the at least one lateral dimension of the contact element to a plurality of positions;
- controlling the optoacoustic sensor to emit electromagnetic radiation while the optoacoustic sensor is being moved or located at the plurality of positions;
- controlling the optoacoustic sensor to detect acoustic waves generated in the object in response to irradiating the object with the electromagnetic radiation while the optoacoustic sensor is being moved or located at the plurality of positions and to generate according detection signals; and
- controlling the processor to generate at least one optoacoustic image based on the detection signals.

16. The probe according to claim 3, wherein the light guide exhibits a core diameter smaller than 350 µm, preferably smaller than 250 µm.

17. The system according to claim 13, the contact surface having a high friction material disposed thereon.

* * * * *